United States Patent [19]

Buchanan et al.

[11] 4,443,431
[45] Apr. 17, 1984

[54] NEISSERIA GONORRHOEAE VACCINE

[75] Inventors: Thomas M. Buchanan, Seattle, Wash.; William Pearce, Arlington, Va.; Kirk C. S. Chen, Seattle, Wash.

[73] Assignee: The United States of America as represented by the Department of Health and Human Services, Washington, D.C.

[21] Appl. No.: 267,538

[22] Filed: May 27, 1981

[51] Int. Cl.$^3$ ................... A61K 39/095; C07C 103/52
[52] U.S. Cl. ........................................ 424/92; 424/88; 260/112 R
[58] Field of Search ................ 424/88, 92; 260/112 R

[56] References Cited

U.S. PATENT DOCUMENTS

| | | | |
|---|---|---|---|
| 4,203,971 | 5/1980 | Buchanon | 424/92 |
| 4,220,638 | 9/1980 | Karkhonis | 421/92 |
| 4,330,623 | 5/1982 | Karkhanis | 424/92 |

OTHER PUBLICATIONS

Terrance G. Cooper, The Tools of Biochemistry, pp. 291-292, (1977).
William A. Pearch and Thomas M. Buchanan, "Attachment Role of Gonococcal Pili," J. Clin. Invest., 61: 931-943, (1978).
Jephcott, et al., "Neisseria Gonorrhoeae III, Demonstration of Presumed Appendages to Cells from Different Colony Types," ACTA Pathol. Microbiol Scand., Section B, 79, 437–439, (1971).
Swanson, et al., "Studies on Gonococcus Infection, I. Pili and Zones of Adhesion: Their Relation to Gonococcal Growth Patterns", Journal of Experimental Medicine, 134, 886–906, (1971).
Buchanan, et al., "Quantitative Determination of Antibody to Gonoccal Pili," Journal of Clinical Investigation, 52, 2896–2909, (1973).
Arko, et al., "Neisseria gonorrhoeae: Effects of Systematic Immunization of Resistance of Chimpanzees to Urethral Infection", Journal of Infectious Diseases, 130 160–164, (1974).
Buchanan, "Antigenic Heterogeneity of Gonococcal Pili," Journal of Experimental Medicine, 141, 1470–1475, (1975).
Buchanan and Pearce, "Pili as a Mediator of the Attachment of Gonococci to Human Erythrocytes", Infection and Immunity, 13, 1483–1489, (1976).
Hermodson, et al., "Neisseria Pili Proteins: Amino-Terminal Amino Acid Sequences and Identification of an Unusual Amino Acid", Biochemistry, 17, 442–445, (1978).
Buchanan, et al., "Pili and Principal Outer Membrane Protein of Neisseria gonorrhoeae: Immunochemical, Structural, and Pathogenic Aspects", Conference Proceedings on Immunobiology of Neisseria Gonorrhoeae, (1978), 145–154, (1978).
Buchanan, et al., "Attachment of Neisseria gonorrhoeae Pili to Human Cells, and Investigations of the Chemical Nature of the Receptor for Gonococcal Pili", Conference Proceedings on Immunobiology of Neisseria Gonorrhoeae, (1978), 242–249, (1978).
Brinton, et al., "Uses of Pili in Gonorrea Control: Role of Bacterial Pili in Disease, Purification and Properties of Gonococcal Pili and Progress in Development of a Gonococcal Pilus Vaccine for Gonorrhea", Conference Proceedings on Immunobiology of Neisseria Gonorrhoeae, (1978), 155–178, (1978).
Pearce and Buchanan, "Optimum Conditions and Quantitation of Adherence of Isolated Pili to Human Cells in Vitro", Journal of Clinical Investigation, 61, 931–943, (1978).
Buchanan, "Prospects and Problems for Development of a Vaccine Against Gonorrhea", Abstract from Embo Workshop on Genetics and Immunobiology of Pathogenic Neisseria, Hemavan, Sweden, (Jun. 1980).
Chen & Buchanan, "Structural Studies of a Gonococcal Pilus", Abstract from Embo Workshop on Genetics and Immunobiology of Pathogenic Neisseria, Hemaven, Sweden (Jun. 1980).

Primary Examiner—Blondel Hazel
Attorney, Agent, or Firm—Holman & Stern

[57] ABSTRACT

A vaccine affording protection against attachment of Neisseria gonorrhoeae (N.g.) to human cells, and consequent infection, is prepared from a fragment of pili protein isolated from gonococci. This fragment contains the shared antigens between pili from different N.g., in an exposed form.

14 Claims, 1 Drawing Figure

NEISSERIA GONORRHOEAE VACCINE

BACKGROUND OF THE INVENTION

1. Field of the Invention

The present invention is directed to a prophylactic vaccine effective against *Neisseria gonorrhoeae* (N.g.) and consequent infection therefrom. Specifically, the instant invention is directed to a fragment of pili protein obtained from gonococci, a method of isolating and purifying same, and a vaccine prepared therefrom.

2. Description of the Prior Art

Gonorrhea is an extremely common infection in humans, and in the United States alone, approximately four million persons annually appear in clinics and physicians offices with this sexually transmitted disease. Despite effective antibiotics, the annual number of cases of gonorrhea in the U.S. has remained essentially unchanged for the past five years. Some gonococci have become resistant to treatment with penicillin, which formerly was one of the most frequently employed medicaments, and there is a growing need for a vaccine to contain this contagion.

Heretofore, no successful vaccine has been available having efficacy against the numerous strains of N.g. One of the principal problems which has impeded the production of a vaccine is the antigenic heterogeneity of the N.g. microorganisms. One of the important N.g. fragments that demonstrates the antigenic heterogeneity are the pili, filamentous structures or hair-like organelles that extend from the surface of virulent N.g. organisms to facilitate their attachment to human cells. Pili were first discovered on N.g. in 1971 (Jephcott, A. E., et al.: Acta Pathol. Microbiol. Scand. Sect. B., 79:437-439, June 1971. "Brief Report: *Neisseria gonorhoeae*. III. Demonstration of Presumed Appendages to Cells from Different Colony Types."; Swanson, J. S., et al.: J. Exp. med., 134:886-906, October, 1971. "Studies on Gonococcus Infection. I. Pili and Zones of Adhesion: Their Relation to Gonococcal Growth Patterns.") and first purified in 1972 and 1973 (Buchanan, T. M., et al.: J. Clin. Invest. 52:2896-2909, Nov. 1973, "Quantitative Determination of Antibody to Gonococcal Pili."). They were subsequently shown to have antigenic heterogeneity (Buchanan, T. M.: J. Exp. Med. 141:1470-1475, June 1975, "Antigenic Heterogeneity of Gonococcal Pili."; Buchanan, T. M. and Pearce, W. A.: Infect. Immun. 13:1483-1489, May 1976, "Pili as a Mediator of the Attachment of Gonococci to Human Erythrocytes."; Brinton, C. C., Jr., et al.: Immunobiol. *Neisseria gonorrhoeae* Proc. Conf. (1978):155-178, Jan. 18-20, 1978, "Uses of Pili in Gonorrhea Control: Role of Bacterial Pili in Disease Purification and Properties of Gonococcal Pili, and Progress in the Development of a Gonococcal Pilus Vaccine for Gonorrhea." Amer. Soc. Microbiol. Wash. D.C., Sept. 29, 1978; Buchanan, T. M., et al.: Immunobiol. *Neisseria gonorrhoeae* Proc. Conf. (1978): 145-154, Jan. 18-20, 1978, "Pili and Principal Outer Membrane Protein of *Neisseria gonorrhoeae*: Immunochemical, Structural, and Pathogenic Aspects." Amer. Soc. Microbiol., Wash. D.C., Sept. 29, 1978; Buchanan, T. M.: J. Infect Dis. 138:319-325, Sept. 1978, "Antigen-Specific Serotyping of *Neisseria gonorrhoeae* I. Use of an Enzyme-Linked Immunosorbent Assay to Quantitate Pilus Antigens on Gonococci." The significance of the pili antigenic heterogeneity was implied in chimpanzees (Arko, R. J., et al.: J. Infect. Dis. 130:160-164, August 1974, "*Neisseria gonorrhoeae*: Effects of Systemic Immunization on Resistance of Chimpanzees to Urethral Infection."), since immunized chimps were protected against a urethral challenge infection if the challenge N.g. organisms contained pili of the same antigenicity as the N.g. organisms in the vaccine, but not if the pili of the vaccine and challenge N.g. were different. Brinton, et al. (1978, supra) used purified whole pili of a single antigenic type to immunize human volunteers, and demonstrated that these volunteers were more protected that non-immunized volunteers when $10^2$ N.g. of the same pili type were introduced into their urethra. However, it has been shown that more than 35 different antigenic types of pili exist on gonococci (Brinton, et al, 1978, supra). Consequently, a vaccine containing only a single pilus antigenic type would be expected to protect against less than 3% of infections with N.g., since antibodies prepared to a single pilus antigenic type only maximally protect against attachment mediated by that same antigenic type of pilus.

The attachment capabilities of isolated gonococcal pili were demonstrated in 1976 (Buchanan & Pearce, 1976, supra) and further characterized in 1978 (Pearce, W. A. and Buchanan, T. M.: J. Clin. Invest. 61:931-943, April 1978, "Attachment Role of Gonococcal Pili: Optimum Conditions and Quantitation of Adherence of Isolated Pili to Human Cells in Vitro."), including initial chemical characterization of the receptor on the human cell surface to which pili bind (Buchanan, T. M., et al.: Immunobiol. *Neisseria gonorrhoeae* Proc. Conf. (1978):242-249, Jan. 18-20, 1978, "Attachment of *Neisseria gonorrhoeae* Pili to Human Cells, and Investigations of the Chemical Nature of the Receptor for Gonococcal Pili." Amer. Soc. Microbiol., Wash, D.C., Sept. 29, 1978.). Also, the amino acid composition of pili of antigen type 33 (Hermodson, M. A., Chen, K. C. S., and Buchanan, T. M.: Biochemistry 17:442-445, Feb. 1978, "Neisseria Pili Proteins: Amino-Terminal Acid Sequences and Identification of an Unusual Amino Acid.") and of antigen type CDC-B (Brinton, et al. 1978, supra), and the amino acid sequence of the first 29 residues of pili antigenic types F62, B, 33, and 7122 were published in 1978 (Hermodson, Chen & Buchanan, 1978, supra).

Despite this significant progress, a successful vaccine to prevent gonorrhea, based upon intact whole pili of N.g. seemed unlikely. This was because it was demonstrated that intact whole pili of a single antigenic type, when used as a vaccine, produce antibody primarily to that single antigenic type, rather than to shared pili antigens (Buchanan, 1975, supra; Buchanan & Pearce, 1976, supra; Brinton, 1978, supra, Buchanan, p242-244, 1978, supra). These antibodies specific to a single pilus antigenic type were maximally effected only against N.g. containing the same pili antigens. Since there are more than 35 different antigenic types of pili, it is impractical to prepare a vaccine of intact whole pili containing enough antigenic types to provide protection against most N.g. that cause gonorrhea.

SUMMARY OF THE INVENTION

This invention affords a cleaved fragment of pili from the bacteria *Neisseria gonorrhoea* having the characteristics, among others, that:

(a) the fragment is cleaved at a methionine group;

(b) the fragment is the largest fragment so obtained;

(c) the fragment has an amino acid sequence which is different than the amino acid sequences of the other fragments;

(d) the fragment contains an antigen common to most pili of *Neisseria gonorrhoeae;* and (e) the fragment is the only fragment capable of binding to cells.

Another object of the present invention is a vaccine for N.g. obtained from the pili protein which contains a single antigen common to pili of all strains of N.g.

It is a further object of the instant invention to provide a method of isolating and purifying a N.g. pili fragment and preparation of a vaccine therefrom which stimulates antibody production effective against all virulent strains of N.g.

By fractionating pili into three fragments, using a procedure described more fully hereinafter, the largest of the three fragments (designated CNI or CNBrI) is found to contain a shared antigen found in all pili of N.g. This antigen is exposed in the fragment, and accessible to stimulate an immune response to the common pili antigen. In fact, almost all of the antibody produced to this fragment is directed to the common pili antigen. This is in marked contrast to antibodies prepared to whole pili, where less than 5% are directed at the common pili antigen. In addition, it has been determined that the CNI fragment retains the capability to bind to cells, whereas the other fragments do not, indicating that the pili attachment site is located on the CNI fragment. It was suggested that the common antigen(s) of pili might be the pili binding site or close to it, since even whole pili that are very different antigenically have identical characteristics of attachment to human and animal cells (Pearce and Buchanan, 1978, supra). This possibility has been confirmed, since antibodies prepared to the CNI fragment of a single antigenic type of gonococcal pili are effective at blocking the attachment of N.g. containing pili of many different antigenic types to human and animal cells. The invention, therefore, is the creation of a fragment of pili, CNI, that contains the pili binding site and shared pili antigen(s), that can stimulate antibodies to the shared antigen(s) that block attachment of piliated gonococci to cells, and consequent infections. The use of this fragment as a vaccine in animals, including primarily humans, will afford broad protection against attachment and infection by a large number of different N.g. strains.

DESCRIPTION OF THE PREFERRED EMBODIMENTS

Figure 1:
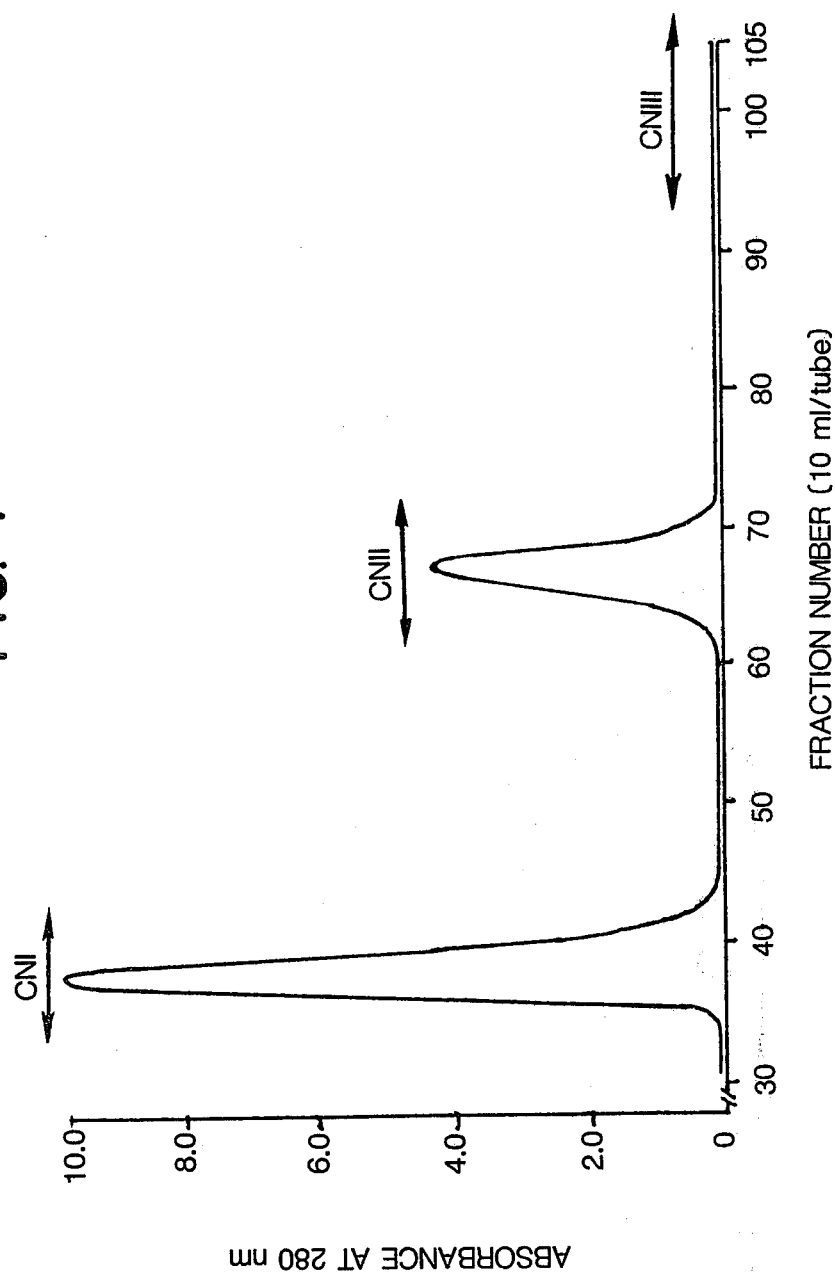

To create the fragments of pili, pili purified according to methods described in Pearce and Buchanan (1978), supra, or Hermodson (1978), supra, were reduced, carboxymethylated and then cleaved using cyanogen bromide. The cyanogen bromide cleaves polypeptide chains at those positions occupied by methionine, leaving homoserine at those sites after cleavage. The method of cleaving pili into fragments is exemplified as follows: 200 mg of purified pili, obtained from F62 strain of N.g., were dissolved in 20 ml of aqueous 6 M guanidine hydrochloride, 2 M Tris-HCl, and 0.01 M EDTA, pH 8.6. The reducing agent, dithiothreitol, was then added yielding a solution having a concentration of 0.1 M with respect to the reducing agent. After being flushed with nitrogen gas, the flask was closed and stirred for three hours at 37° C. to complete the reduction of pili. Carboxymethylation was accomplished by then adding iodoacetic acid (three times recrystallized from n-hexane) to the flask to a final concentration with respect thereto of 0.22 M, and continuing the reaction in the dark, at room temperature, for 15 minutes. This mixture was then dialyzed against 100 volumes of distilled water thoroughly bubbled with nitrogen at 4° C., and with four changes of the water, for 36 hours, The dialyzed, reduced and carboxymethylated pili were then lyophilized, and 160 mg of reduced and carboxymethylated pili were dissolved in 16 ml of 70% formic acid. To this solution, 160 mg of cyanogen bromide (CNBr) was added to cleave the pili into fragments, and the reaction mixture was maintained at room temperature for 20 hours in the dark. At the end of this period, the mixture was diluted with a ten-fold excess of water, and lyophilized. The lyophilized cyanogen bromide fragments from the carboxymethylated pili were dissolved in 16 ml of 6 M urea (prepurified by passage sequentially through a column of Dowex 50W—a trademark of Dow Chemical Co. for an ion exchange resin composed of sulfonated polystyrene cross-linked to divinyl benzene—in the H+ form, and a column of Dowex 1—a trademark of Dow Chemical Co. for an ion exchange resin of a quaternary amine-divinyl benzene, in the OH− form), 0.2 M of a buffering system composed of tris(hydroxymethyl aminomethane) (referred to hereinafter by its common name Tris) and HCl, pH 7.0. This solution was loaded onto a 2.5×255 cm column of Sephadex G-75 (trademark of Pharmacia Chemical Co. for a molecular sieve composed of dextran cross-linked with epichlorohydrin to a bead-formed gel, having a molecular sieve exclusion limit of approximately 80,000 Daltons for peptides and globular proteins) preequilibrated with 6 M urea (prepurified), 0.2 M Tris-HCl, pH 7.0, and eluted with the same urea-Tris-HCl buffer. The peptide fragments in the eluate were detected by absorbance at 280 nM, and eluted as two major and one minor peak, as shown in the FIGURE (Chen, K. C. S., and Buchanan, T. M.: Proc. EMBO Workshop on Genetics and Immunobiology of Pathogenic Neisseria (Hemavan, Sweden 1980): Abstract 31, June 16–19, 1980. "Structural Studies of a Gonococcal Pilus."). The largest fragment, comprising approximately 60% of the subunit of strain F62 N.g. pili, based on the number of amino acids in the subunit, was eluted first from the column and was termed CNI or CNBrI (referring to the cyanogen bromide used to produce the fragment and the fact that it eluted first from the column). The second fragment peak, approximately 32% of the subunit, was termed CNII, and a final small fragment of only 7 amino acids was termed CNIII (FIG. 1).

The CNI and CNII fragments were tested, chemically, and for antigenicity and their capability to bind to human cells. Antibodies were produced in rabbits and subsequent testing was done on human cells in vitro, on piliated organisms and on antibodies. Only the CNI fragment contained shared pili antigens and bound to human and animal cells. Chemical studies showed the CNI fragment of pili from strain F62 N.g. to have an amino acid composition as shown in Table 1, and an amino acid sequence as shown in Table 2. Both Table 1 and Table 2 employ conventional amino acid abbreviations.

TABLE 1

Amino Acid Composition of the CNI Fragment of Pili from Strain F62 of *Neisseria Gonorrhoeae*[a]

| Asx 8 | Val 10 |

TABLE 1-continued

**Amino Acid Composition of the CNI Fragment of Pili from Strain F62 of *Neisseria Gonorrhoeae*\***

| | |
|---|---|
| Thr 7 | Ile 7 |
| Ser 5 | Leu 8 |
| Hse 1.6 | Tyr 5 |
| Glx 9 | Trp 1 |
| Pro 3 | Lys 5 |
| Gly 7 | His 2 |
| Ala 15 | Arg 2 |

*The numbers in the table refer to the actual number of amino acids within the fragment, within experimental error.

TABLE 2

**Amino Acid Sequence of the CNI fragment of Pili from Strain F62 of *Neisseria gonorrhoeae***

| CNIII | 1 | | | | 5 | | | | | 10 | CNI |
|---|---|---|---|---|---|---|---|---|---|---|---|
| | N—Me-Phe | Thr | Leu | Ile | Glu | Leu | Met | Ile | Val | Ile | |
| | 11 | | | | 15 | | | | | 20 | |
| | Ala | Ile | Val | Gly | Ile | Leu | Ala | Ala | Val | Ala | |
| | 21 | | | | 25 | | | | | 30 | |
| | Leu | Pro | Ala | Tyr | Gln | Asp | Tyr | Thr | Ala | Arg | |
| | 31 | | | | 35 | | | | | 40 | |
| | Ala | Gln | Val | Ser | Glu | Ala | Ile | Leu | Leu | Ala | |
| | 41 | | | | 45 | | | | | 50 | |
| | Glu | Gly | Gln | Lys | Ser | Ala | Val | Thr | Glu | Tyr | |
| | | | | | 90 | | | | | 95 | |
| | | | Ser | Val | Thr | Val | Thr | Asp | Gly | | |
| | 96 | | | | 100 | | 102 | | | 105 | CNII |
| | Val | Val | Thr | Ala | Lys | Met | Ala | Ser | Ser | Asn | |
| | 106 | | | | 110 | | | | | 115 | |
| | Val | Asn | Lys | Glu | Ile | Gln | Asn | Lys | Leu | Ser | |
| | 116 | | | | 120 | | | | | 125 | |
| | Leu | Trp | Ala | Lys | Arg | Glu | Asp | Gly | Ser | Val | |
| | 126 | | | | 130 | | | | | 135 | |
| | Lys | Trp | Phe | CMC | Gly | Gln | Pro | Val | Thr | Arg | |
| | 136 | | | | 140 | | | | | 145 | |
| | Lys | Thr | Gly | Asp | Asp | Asp | Asp | Thr | Val | Ala | |
| | 146 | | | | 150 | | | | | 155 | |
| | Lys | Glu | Ile | Lys | Asn | His | Leu | Pro | Ser | Thr | |
| | 156 | | | | 160 | | 163 | | | | |
| | CMC | Arg | Asp | Lys | His | Asp | Ala | Lys | | | |

The exact antigen site and possibly the exact amino acid sequence of CNI and CNII has not yet been determined. However, the site and possibly the sequence will be the same for all pili fragments and therefore is inherently disclosed by the other stated characteristics. The sequence given for the CNII fragment has been determined but has not yet been confirmed.

The elucidation of the amino acid sequence of the CNI and CNIII fragments of the F62 stain of N.g. was performed with a JEOL model JLC-6AH Amino Acid Analyzer according to the procedure of Spackman D. H., Stein W. H. and Moore S. "Automatic Recording Apparatus for Use in the Chromatography of Amino Acids", Analytical Chemistry, 30:1190–1207 (1958). The sequence of the amino acids was determined by the method of Chen K. C. S., Kindt T. J., and Krause R. M., "Primary Structure of the L Chain from a Rabbit Homogeneous Antibody to Streptococcal Carbohydrate Purification of the Antibody and Sequence Determination of Peptides from α-Chymotryptic and Thermolytic Digests" Journal of Biological Chemistry, 250:3280–3288 (1975). Tryptophan determinations were performed according to the method of Liu T. Y. and Chang Y. H., "Hydrolysis of Proteins with p-Toluenesulfonic Acid", Biological Chemistry, 246:2842–2848 (1971).

Rabbits were immunized with CNI fragments of pili from strain F62 N.g., or with CNI fragments of two antigenically different pili of N.g., strains 33 and MEL. In each instance the CNI fragments were highly immunogenic and produced approximately 100 fold higher amounts of antibody to CNI fragments than immunization with whole intact pili of the same strain of N.g. which was used to prepare the CNI fragments. In addition, antibodies produced to CNI fragments of any of the three antigenically different pili used reacted equally well with CNI fragments from each of the other antigenically different pili. This indicated that antigens on the CNI fragment were common to the three pili, even though the intact whole pili were very different antigenically as reported previously (Buchanan & Pearce, 1976, supra; Buchanan, 1978, supra). This common antigenicity shared by the CNI segments from the three antigenically different pili was further documented by radioimmunoassay and summarized in Table 3 (Buchanan, T. M., Siegel, M. S., Chen, K. C. S., and Pearc, W. A.: Seminars in Infectious Diseases, In Press 1981, Proc. Symposium on Bacterial Vaccines, Bethesda, Md., Sept. 1980, "Development of a Vaccine to Prevent Gonorrhea".)

TABLE 3

Radioimmunoassay for Shared Pili Antigens

| Inhibitor (Serotype)* | Amt. in Nanograms | % Inhibition** |
|---|---|---|
| Whole pili (1) | 30 | 64 |
| Whole pili (2) | 30 | 57 |
| Whole pili (3) | 30 | 37 |
| CNBrI (1) | 100, 10 | 65, 28 |
| CNBrI (2) | 100, 10 | 60, 36 |
| CNBrI (3) | 100, 10 | 55, 37 |

*Three antigenically different pili were used, designated serotypes (1), (2), and (3).
**Percent inhibition of the radioimmunoassay was directly related to the antigenicity. The more antigenic the product, the more inhibition it produced in the RIA.

Several monoclonal antibodies were produced to the CNI fragment of pili of strain F62 of N.g., and these antibodies reacted with each of ten different piliated N.g. These data indicate that the CNI contains an antigen(s) common to most, if not all, pili of N.g., and this antigen is exposed and accessible on the CNI fragment. The CNI fragment of pili attach to cells with the identical characteristics as previously reported for whole intact pili, including the optimum PH range for attachment and inhibition with gangliosides. It has been previously noted that pili and the amino terminal fragment (CNBrI, CNI) attach best to the parent cell and the carboxyterminal fragment (CNBrII, CNII) does not attach to any of the cells (Gubish, E. R., Pearce, W. A., Chen, K. C. S., and Buchanan, T. M.: Abstract B81, 81st Annual Meeting American Society for Microbiology, Mar. 1-6, 1981.) These data strongly suggest that the site on the pili responsible for binding to human cell surface receptors is located on the amino terminal portion of the pilus subunit and that this site is resistant to the denaturing conditions of cyanogen bromide.

Thus, the preceding results represent the first known demonstration of (1) a chemical procedure to create fragments of pili using cyanogen bromide and a method to effectively separate the largest (CNI) fragment from the other fragments; (2) the fact that shared pili antigen(s) are found in an exposed accessible form on the CNI fragment; (3) the fact that the pili binding site resides on the CNI fragment at, or near, the location of the shared antigen(s) among pili of N.g.; and (4) the fact that CNI fragment, with the amino acid composition and amino acid sequence shown in Tables 1 and 2, can stimulate an antibody response and these antibodies can block the attachment of many different N.g. to cells, even when the pili on these N.g. are of many different antigenic types.

The use of the CNI fragment of pili as a vaccine to prevent gonorrhea is illustrated as follows. The purified CNI is desalted to rid the fraction of Tris and urea by means of a Sephadex G-25 column (trademark of Pharmacia Chemical Co. for dextran cross-linked with epichlorohydrin to a bead-forming gel, having a molecular sieve exclusion limit of approximately 5,000 Daltons), preequilibrated in and eluted with 0.05 M $NH_4OH$. This CNI fraction is then lyophilized, and the white powder obtained thereby is resuspended in sufficient phosphate buffered saline to provide a concentration of 0.5-2.0 mg/ml of pili protein. It is possible to add serum albumin in order to reduce protein-protein interactions and form thereby smaller particles. When preparing a human vaccine, human serum albumin is preferably added, thus avoiding the production of antibodies to it. When the latter is employed, it is used at a concentration of 0.5 mg/ml. This solution is then filter sterilized by passage through a $0.22\mu$ membrane filter, such as a Millipore filter. This preparation is then packaged as a solution in sterile containers, and the packaged vaccine lot is tested for sterility, safety in guinea pigs and mice and for pyrogenicity as required by the F.D.A. Such preparations pass the above tests.

The vaccine according to the present invention may, be administered by conventional techniques, including interperitoneal, intradermic, intravascular, and intravenous injection and oral administration. However, intramuscular and subcutaneous injection and local injection or topical application at the site of potential infection appear to provide the most efficacious methods of administering the vaccine, particularly in humans. When the vaccine is administered by the above-identified preferred methods, dosage is approximately 100 to 500 $\mu$g protein, with or without an adjuvant, such as aluminum hydroxide gel. The antibodies produced inhibit attachment of most piliated gonococci to human cells, and the consequent gonorrhea infection.

We claim:

1. A cleaved fragment of purified pili protein from *Neisseria gonorrhoeae* comprising a CNI fragment which is the largest fragment obtained by cleavage of the purified pili protein at the methionine residues thereof, said fragment being further characterized by:
   (a) an amino acid sequence different from the amino acid sequences of the other fragments;
   (b) containing an antigen common to most pili of *Neisseria gonorrhoeae;* and
   (c) being the only fragment obtained capable of binding to cells.

2. The cleaved fragment of claim 1, wherein said fragment is characterized by stimulating in mammals antibody production to at least one antigen common to pili of most strains of *Neisseria gonorrhoeae.*

3. A vaccine for protecting animals against *Neisseria gonorrhoeae* infection consisting essentially of an effective amount of the cleaved fragment of claim 1 admixed with a pharmaceutically acceptable carrier.

4. The vaccine of claim 3 in admixture with a pharmaceutically acceptable adjuvant.

5. The vaccine of claim 4, wherein said pharmaceutically acceptable adjuvant is an aluminum hydroxide gel.

6. The vaccine of claim 3, wherein the vaccine contains a concentration of said fragment of 0.5 to 2.0 mg/ml.

7. A method of protecting mammals against infection by *Neisseria gonorrhoeae* microorganisms comprising administering an immunologically effective amount of the vaccine of claim 3 to a mammal.

8. The method of claim 7, wherein the mammal being protected is a human.

9. The method of claim 8, wherein the vaccine is administered intramuscularly.

10. The method of claim 8, wherein the vaccine is administered subcutaneously.

11. The method of claim 8 or claim 10, wherein the vaccine is administered in an amount containing 100 to 500 micrograms of pili protein.

12. The method of claim 8, wherein the vaccine is administered locally.

13. The method of claim 12, wherein the vaccine is injected at the site of infection.

14. The method of claim 11, wherein the vaccine is applied topically.

* * * * *